(12) United States Patent
Ann et al.

(10) Patent No.: US 6,383,528 B1
(45) Date of Patent: May 7, 2002

(54) PHARMACEUTICAL COMPOSITION COMPRISING TICLOPIDINE AND GINKGO BILOBA EXTRACT

(75) Inventors: Hyung Soo Ann; Hye Sook Yun-Choi; Yeong Shik Kim, all of Seoul; Yong Oh Lee; Kyung Hee Lee, both of Kyungki-do; Sung An Kang, Seoul, all of (KR)

(73) Assignee: Yuyu International Co., Ltd., Kyungki-Do (KR)

( * ) Notice: Subject to any disclaimer, the term of this patent is extended or adjusted under 35 U.S.C. 154(b) by 0 days.

(21) Appl. No.: 09/581,789

(22) PCT Filed: Feb. 27, 1998

(86) PCT No.: PCT/KR98/00036
§ 371 Date: Aug. 10, 2000
§ 102(e) Date: Aug. 10, 2000

(87) PCT Pub. No.: WO99/32131
PCT Pub. Date: Jul. 1, 1999

(30) Foreign Application Priority Data

Dec. 23, 1997 (KR) .............................................. 97-72848

(51) Int. Cl.⁷ ................................................. A01N 65/00
(52) U.S. Cl. ........................ 424/752; 514/277; 514/279; 514/280
(58) Field of Search ............................... 424/195.1, 752; 514/277, 279, 280

(56) References Cited

U.S. PATENT DOCUMENTS 4,734,280 A * 3/1988 Braquet .................... 424/195.1
5,134,149 A * 7/1992 Carr et al. .................. 514/317
5,322,688 A * 6/1994 Schwabe .................. 424/195.1

OTHER PUBLICATIONS

Yim et al. J. Toxicol. Public Health. vol. 14, No. 1, pp. 119–122, abstract enclosed, Jan. 1998.*
Kim et al. Thrombosis Res. vol. 91, No. 1, pp. 33–38, abstract enclosed, Jul. 1998.*
Trouve et al. FASEB Journal. vol. 10, No. 3, p. A43 (Abstract No. 246), Apr. 1996.*

* cited by examiner

*Primary Examiner*—Christopher R. Tate
(74) *Attorney, Agent, or Firm*—Lowe Hauptman Gilman & Berner, LLP

(57) ABSTRACT

The invention herein relates to a pharmaceutical composition comprising ticlopidine and Ginkgo biloba extract. In detail, as an anti-thrombotic preparation, the pharmaceutical composition comprising said ticlopidine and Ginkgo biloba extract with the PAF-antagonistic and anti-oxidant actions is used in combination to naturally suppress the neutropenia and agranulocytosis caused by the toxicity resulting from the repeated use of ticlopidine alone.

8 Claims, 6 Drawing Sheets

* P<0.05 : Shows significant difference from the control group
# P<0.05 : Shows significant difference from the ticlopidine group Control Ticlopidine administration group Ticlopidine and Gingko biloba extract administration group (5:1)

Ticlopidine and Gingo biloba extract administration group (5:2)

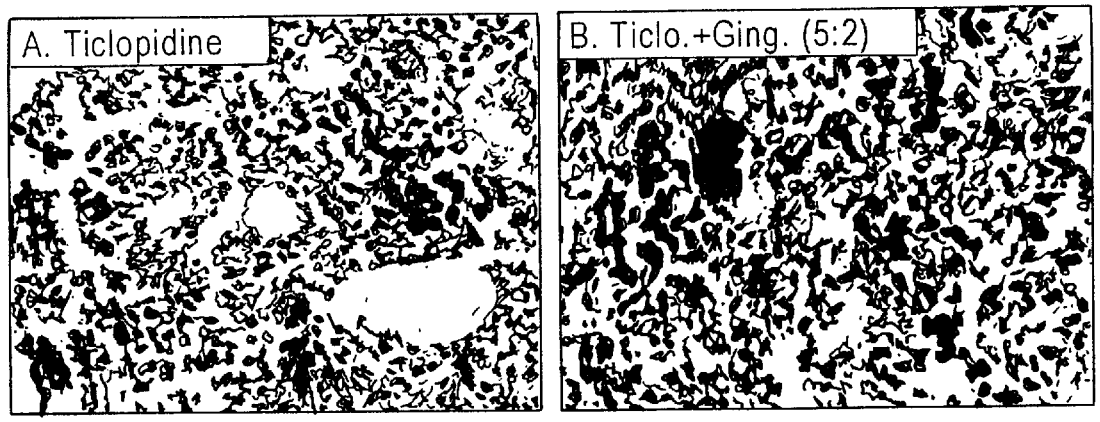
Control | Ticlopidine and Gingko biloba administration group (5:2)
FIG. 4(A) | FIG. 4(B)

** P<0.05 : Shows significant difference from the control group
# P<0.05 : Shows significant difference from the ticlopidine group

* P<0.05 : Shows significant difference from the control group
# P<0.05 : Shows significant difference from the ticlopidine group

PHARMACEUTICAL COMPOSITION COMPRISING TICLOPIDINE AND GINKGO BILOBA EXTRACT

FIELD OF THE INVENTION

The invention herein relates to a pharmaceutical composition comprising ticlopidine and Ginkgo biloba extract. In detail, as an anti-thrombotic preparation, the pharmaceutical composition comprising said ticlopidine and Ginkgo biloba extract with the PAF-antagonistic and anti-oxidant actions is used in combination to naturally suppress the neutropenia and agranulocytosis caused by the toxicity resulting from the repeated use of ticlopidine alone.

BACKGROUND OF THE INVENTION

As a platelet aggregation inhibitor belonging to the thienopyridine group, ticlopidine is widely used clinically. Unlike aspirin, ticlopidine does not affect the production of prostacycline-thromboxane $A_2$. Further, metabolites such as 2-hydroxyticlopidine (2-HT) inhibit the platelet aggregation induced by ADP, collagen, arachidonic acid, thrombin, or PAF, which in turn stimulate the expression of the glycoprotein IIb/IIIa receptors on platelets. Glycoprotein IIb/IIIa, a fibrinogen receptor on the plasma membrane of platelets, is required for the formation of a plug via platelet aggregation. By suppressing the expression of the glycoprotein IIb/IIIa receptors, ticlopidine inhibits the platelet aggregation therein. Consequently, the suppression is put to an effect as if the platelets were in anesthesia.

Further, ticlopidine decreases the viscosity of blood by means of reducing fibrinogen in the plasma in conjunction with an increase in the plasticity of the red blood cells.

As such, ticlopidine is a synthetic drug which suppresses the functions of the platelets. The drug is widely used for the purposes of clinically preventing a stroke coupled with thrombosis and arteriosclerosis, ischemic heart diseases such as angina, intermittent claudication, etc.

However, if ticlopidine is repeatedly used by itself, the problem arises in which the major side-effects are reversible neutropenia and agranulocytosis. Neutropenia is defined as neutrophil counts in blood falls below $1200/mm^3$. Agranulocytosis is defined as neutrophil counts in blood falls below $450/mm^3$.

Aforementioned toxicity manifests in the patients at the incidence rate of 0.8% during the first 3 months of treatment. Although the granulocyte, colony-stimulating factor can be used to improve the situation, this cannot be the fundamental solution. Consequently, aspirin is used as a primary drug for a stroke, etc, and ticlopidine is used as a secondary drug in the case of patients who are intolerant to aspirin.

In worsening condition, ticlopidine may cause bone-marrow toxicity with the result of thrombocytopenia, which in return causes purpura or prolongation in hemorrhage period. The problem can be further complicated by the manifestation of aplastic anemia.

On the other hand, in the case of clozapine with respect to the similar problem of neutropenia as in ticlopidine, L-ascorbic acid which is an anti-oxidant has been used in combination to improve the situation. [Korea Patent Application No. 97-700915] However, this method is not preferable since L-ascorbic acid only has the anti-oxidant action without increasing the effect of clozapine.

SUMMARY OF THE INVENTION

In order to solve various problems when ticlopidine is used alone as an anti-thrombotic preparation, the Ginkgo biloba extract with anti-oxidant action and platelet aggregation inhibition effect are used in combination with said ticlopidine. As such, the objective of the present invention is to provide a new pharmaceutical composition comprising ticlopidine and Ginkgo biloba extract, which has the effect of decreasing neutropenia toxicity in addition to improving the inhibition of platelets aggregation.

BRIEF DESCRIPTION OF THE DRAWINGS

FIG. 4 is the photograph (×400) of the histology of the femur osteoepiphysis marrow cells of the white mice after 16 weeks of treatment in which ticlopidine is used alone or in combination (5:2) with the Ginkgo biloba extract followed by two weeks of withdrawal.

DETAILED DESCRIPTION OF PREFERRED EMBODIMENTS

Figure 1:
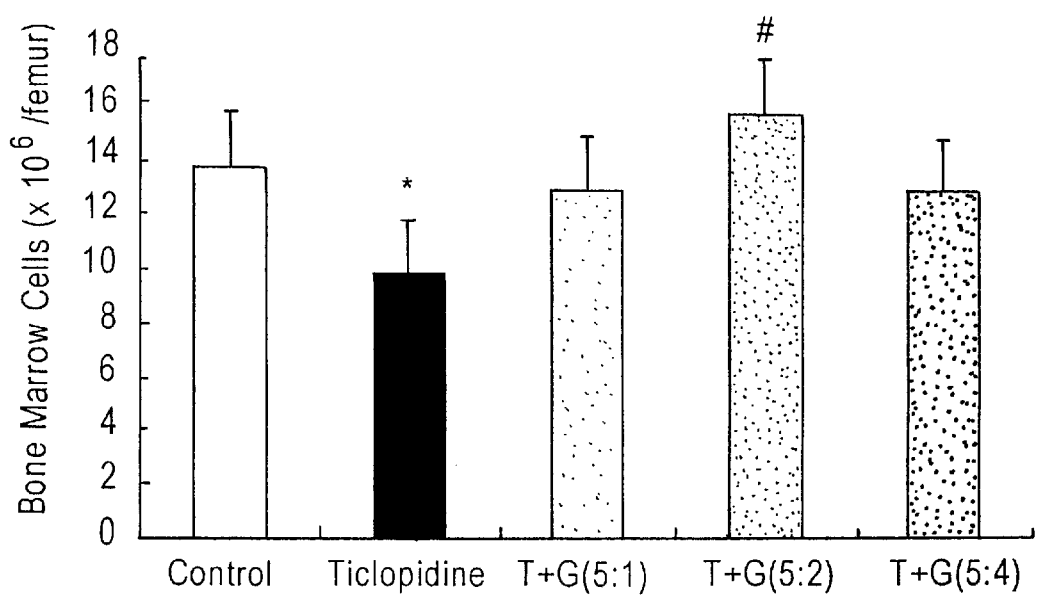
FIG. 1 is the graph showing the effects of the single use of ticlopidine, and the combination use of ticlopidine and Ginkgo biloba extract on the number of femur marrow cells of the rats during the 16-week period.

The invention herein relates to the pharmaceutical composition comprising ticlopidine and Ginkgo biloba extract. In particular, the invention relates to said pharmaceutical composition, which is used as an anti-thrombotic preparation, with the active ingredients of ticlopidine and Ginkgo biloba extract.

The invention herein is explained in more detail as follows: The present invention relates to the pharmaceutical composition comprising ticlopidine and Ginkgo biloba extract with PAF-antagonistic and anti-oxidant actions. The pharmaceutical composition herein serves as an anti-thrombotic preparation in order to ameliorate neutropenia and agranulocytosis caused by the single usage of ticlopidine.

Under said invention, ticlopidine(5-[(2-chlorophenyl) methyl]-4,5,6,7-tetrahydrothieno[3,2-C]pyridine) belongs to the thieneo-pyridine group and is widely used as a platelet aggregation inhibitor due to its anti-thrombotic property. Ticlopidine herein suppresses the expression of the glycoprotein IIb/IIIa, which is the fibrinogen receptor at the platelet plasma membrane, thereby suppressing the aggregation of the platelets caused by ADP. Further, said ticlopidine inhibits the platelet aggregation by collagen, arachidonic acid, thrombin, and PAF as if the platelets were in anesthesia. In short, said ticlopidine is deemed to have the anti-thrombotic effect therein. Ticlopidine decreases the viscosity of blood by reducing the fibrinogen in plasma and has the effect of improving the plasticity of the red blood cells. Despite these advantages, the problems still remain with respect to the reduction of neutrophils. agranulocytosis, etc.

Consequently, the invention herein is characterized by the pharmaceutical composition comprising said ticlopidine and an adequate amount of Ginkgo biloba extract for the purposes of improving the suppression effect on the platelet aggregation while solving the aforementioned problems.

Under said invention, Ginkgo biloba extract, are used, which are produced by the method generally known to a person having ordinary skill in the art to which said subject matter pertains. It is preferable to use the Ginkgo biloba extract containing more than 15 weight % of flavon-glycoside, terpene-lactone, and alkyl-phenol compounds.

The Ginkgo biloba extract obtained from such procedure are generally known to contain flavon-glycoside with the anti-oxidant and cell protection effects. It is reported that the Ginkgo biloba extract containing terpene-lactone has the suppression effect on the platelet aggregation via PAF and ADP in addition to the blood vessel diastolization and cardiovascular effects.

It is hypothesized that the Ginkgo leaf extract has the effect of improving the condition of neutropenia and agranulocytosis through its anti-oxidant property. In other words, when ticlopidine and Ginkgo biloba extract are used in combination, the free radicals of reactive metabolites, such as peroxide anions induced by ticlopidine, are effectively removed. Under such condition, there is a lack of covalent bonds among nucleophiles, namely protein and glutathione, derived from the marrow peroxidase and white blood cell, with the result of significantly reducing neutropenia and agranulocytosis.

Under said invention, the Ginkgo biloba extract in the composition contain 10~240 weight parts to 100 weight parts of ticlopidine. The Ginkgo biloba extract are administered in the amount of 40 mg~480 mg daily, or preferably 80 mg~240 mg. If the portion of Ginkgo biloba extract fall below 10 weight parts, the target effect under said invention is not achieved in any significant way. If more than 240 weight parts are used, which exceed the recommended usage amount, other undesirable side-effects may come about therefrom. On the other hand, if the daily dosage amount is less than 40 mg, no significant effect results therefrom. If more than 480 mg is used, which exceed the recommended usage amount, other undesirable side-effects may result therefrom.

The pharmaceutical composition under said invention can be administered via intestinum, i.e., oral administration. In particular, said composition can be formulated into a dosage in the form of tablet, vesicant, granules, or capsule. At this point, the administration dosage includes the designated amounts of ticlopidine and Ginkgo biloba extract-in addition to a diluent, carrier, and adjuvant, which are ordinarily used in the pharmaceutical preparation. For example, the tablet may include an activation filler, granules, diluent, binders, resolvant, lubricant, stabilizer, pigment, sweetener, or flavors.

The unit dosage amount of the formulation prepared above should contain 50 mg~600 mg of ticlopidine, or preferably 100 mg~250 mg. The unit dosage amount of the Ginkgo biloba extract should be 20 mg~240 mg, or preferably 40 mg~120 mg. The daily administrations of the pharmaceutical composition under said invention are dependent on the administration method or treatment condition, but it is preferable to administer 1~4 times a day for an adult in the case of oral administration.

The pharmaceutical composition comprising ticlopidine and Ginkgo biloba extract so manufactured poses no problems with respect to neutropenia and agranulocytosis even after a repeated usage. Further, the composition, in effect, acts as anti-thrombotic and anti-embolic agents via the anti-thrombotic effect of ticlopidine without any side-effects such as cytotoxicity.

The invention herein will be explained in more detail based on the following examples without limitations thereby.

EXAMPLE OF PREPARATION 100 g of Ginkgo biloba extract in a dry powder form was placed in a centrifuge tube. 930 ml of 60 v/v % acetone in aqueous solution was added so that the Ginkgo biloba leaves powder was effectively infused. After 12 hours, the solution was filtered under reduced pressure, and the filtrant under reduced pressure was concentrated to 150 ml. Thereafter, water was added to make the solution to 200 ml, followed by a vigorous mixing. Then, the solution was cooled for 12 hours at 15° C., after which the supernatant and precipitant were filtered for separation.

During stirring, 50 g of ammonium sulfate was added. After 15 minutes, 37 ml, of methylethylketone and 25 ml, of acetone were added thereto. Then, the organic solvent layer were extracted and separated 3 times with the one-to-one mixed solution of methylethylketone and acetone. The solution was concentrated under reduced pressure to such point that the total amount of the layer of methylethylketone and acetone was equivalent to 10 g. 68 ml, of 50 v/v % ethanol solution was added to said concentrate and dissolved, after which the solution was filtered under 4 atm of pressure with the Diaplo (R) Ultrafiltration layer (Amicone Co., USA).

Then, the filtrate was concentrated to 5 g under reduced pressure and dissolved with 25 ml of the 90 v/v % ethanol solution. The solution was stored for one day at room temperature. Then, the solution was filtered till clear and dried under reduced pressure within the maximum temperature of 60° C. As a result, 2.16 g if the active ingredient (yellow powder) was obtained.

Example 1

Tablet

With the Ginkgo biloba extract from said preparation example, and ingredients and contents in Table 1, the tablet was manufactured by means of a commonly used method for oral administration. In particular, said ingredients were well-mixed and made into an individual tablet via compression.

TABLE 1

| Composition | Amount (mg) |
| --- | --- |
| Ticlopidine hydrochloride | 200 |
| Ginkgo biloba leaves extract | 80 |
| Microcrystalline Cellulose | 60.9 |
| Corn Starch | 28 |
| Colloidal Silicon dioxide | 8 |
| Croscarmellose sodium | 16 |
| Anhydrous citric acid | 3.1 |
| Polyvinyl pyrrolidone K30 | 2 |

TABLE 1-continued

| Composition | Amount (mg) |
|---|---|
| Magnesium stearate | 2 |
| Opadry White | 10 |
| Total Weight | 410 |

Example 2

Vesicant

With the Ginkgo biloba extract from said preparation example, and ingredients and contents in Table 2, the vesicant was manufactured by means of a commonly used method for oral administration. In particular, said ingredients were well-mixed and made into an individual tablet via compression.

TABLE 2

| Composition | Amount (mg) |
|---|---|
| Ticlopidine hydrochloride | 200 |
| Ginkgo biloba leaves extract | 80 |
| Glucose | 1,570 |
| Anhydrous citric acid | 660 |
| Sodium bicarbonate | 445 |
| Polyethylene glycol 6000 | 45 |
| Total Weight | 3,000 |

Example 3

Granules

With the Ginkgo biloba extract from said preparation example, and ingredients and contents in Table 3, the granules were manufactured by means of a commonly used method for oral administration.

TABLE 3

| Composition | Amount (mg) |
|---|---|
| Ticlopidine hydrochloride | 200 |
| Ginkgo biloba leaves extract | 80 |
| Microcrystalline cellulose | 440 |
| Corn starch | 200 |
| D-Mannitol | 640 |
| Sucrose | 426.9 |
| Anhydrous citric acid | 3.1 |
| Magnesium stearate | 10 |
| Total Weight | 2,000 |

Example 4

Capsule

With the Ginkgo biloba extract from said preparation example, and ingredients and contents in Table 4, the capsules were manufactured by means of a commonly used method for oral administration.

TABLE 4

| Composition | Amount (mg) |
|---|---|
| Ticlopidine hydrochloride | 200 |
| Ginkgo biloba leaves extract | 80 |
| Microcrystalline cellulose | 28 |
| Corn Starch | 22 |

TABLE 4-continued

| Composition | Amount (mg) |
|---|---|
| Colloidal Silicon dioxide | 23.6 |
| Croscarmellose sodium | 11.4 |
| Anhydrous citric acid | 3.1 |
| Magnesium stearate | 1.9 |
| Total Weight | 370 |

Experiment 1

Ex Vivo Platelet Aggregation Suppression Effect 50, 100 or 200 mg/kg/day of ticlopidine were administered to female rats during the 3-day period. To 50 mg/kg of ticlopidine, the Ginkgo biloba extract in the proportion of 80% of ticlopidine (i.e., T:G=5:4) or 40 mg/kg of the same were administered. One hour after the final administration on the specimen, the rats were anesthetized. For preventing blood coagulation, the blood sample was collected using a syringe with the anti-coagulant, 3.8% Sodium Citrate solution. Thereafter, the effects oil the platelet aggregation induced by $1 \times 10^{-5}$ M ADP were studied. The results are shown in Table 5.

TABLE 5

| Treatment | Dosage (mg/kg/day) | Number of Rats | Suppression Rate (%) (Avg + SD) |
|---|---|---|---|
| Ticlopidine (T) | 200 | 7 | 97.97 ± 4.53* |
| Ticlopidine (T) | 100 | 7 | 67.06 ± 16.25* |
| Ticlopidine (T) | 50 | 7 | 65.64 ± 10.3* |
| T + Ginkgo biloba extract | 50 + 40 | 7 | 95.95 ± 8.36* |
| Ginkgo biloba extract (G) | 40 | 7 | 54.19 ± 14.48* |
| Aspirin | 50 | 7 | 43.92 ± 13.80* |

Note:
*Where P < 0.05, there is a statistical significance.

When 200 mg/kg of ticlopidine was administered alone, the platelet aggregation induced by ADP was suppressed 98%. When the ticlopidine dosages were reduced to 100 mg/kg and 50 mg/kg, the suppression rates were 67% and 65%, respectively When 50 mg/kg of ticlopidine and 40 mg/kg of Ginkgo biloba extract were administered in combination, the 95% suppression rate of platelet aggregation was shown, which is 1.5 times more effective than the singular administration of ticlopidine. The administration in combination showed a similar effect in terms of deterring platelet aggregation as shown in the case where 200 mg/k of ticlopidine were administered.

Experiment 2

An Increase in Recovery Rate in the Mouse Acute Thrombus Model

The regimen comprising ticlopidine and Ginkgo biloba extract was administered onto the mouse during the 3 day period. One hour after the final administration of the regimen, the mixed solution containing collagen and epinephrine (collagen 1100 μg+epinephrine 110 μg/10 ml of saline solution/kg) was injected into the vein in the tail. The status of paralysis or death from pulmonary infarction, and the recovery therefrom were duly recorded. The results are shown in Table 6.

TABLE 6

| Treatment | Dosage (mg/kg/day) | Number of Mouse | Recovered Mouse Number of Mouse | % |
|---|---|---|---|---|
| Control | — | 10 | 2 | 20 |
| Ticlopidine (T) | 50 | 16 | 6 | 38 |
| Tielopidine (T) | 100 | 15 | 7 | 47 |
| T + Ginkgo biloba Extract (5:2) | 50 + 20 | 14 | 6 | 43 |
| T + Ginkgo biloba Extract (5:4) | 50 + 40 | 14 | 10 | 71 |

As in the experiment above if the mixed solution comprising collagen and epinephrine was infected into the vein a large of amount of thrombus was generated shortly thereafter with the result of an occlusion in the pulmonary artery. Within one minute after the injection, almost every part of the body was in paralysis with the enlargement of a pupil. Dyspnea occurred followed by a seizure. Within 5 minutes, approximately 70~80% of the mouse were deceased. As to the remainder, almost every mouse were dead within 15 minutes or in a continued paralysis. As shown in Table 6, only 20% of the mouse in the control group recovered with free movement within 15 minutes. However, in the case where 50 mg/kg or 100 mg/kg of ticlopidine was administered alone, the recovery rates of 38% and 47% were shown, respectively, which confirmed the anti-thrombotic effect in the acute thrombus model with ticlopidine administration. Further, when 50 mg/kg of ticlopidine, and 20 mg/kg or 40 mg/kg of Ginkgo biloba extract were administered in combination, the recovery rates of 43% and 71% were recorded, respectively, which were higher recovery rates than that in the individual administration.

Experiment 3

Thrombus Formation by Arterio-Venous Shunt (A-V Shunt hereinafter) and the Effects on the Platelet Aggregation The first regimen of 50 or 100 mg/kg of ticlopidine, and the second regimen of 50 mg of ticlopidine and 20 (5:2) or 40 mg (5:4) of Ginkgo biloba extract were administered in combination on female rats during the 9-day period. Thereafter, Table 7 was tabulated with the measured weights of the thrombus formation at the cotton thread in the A-V Shunt. At this point, the weights of thrombus were measured in terms of the wet weight immediately after the experiment, and dry weight after complete drying. From the weights of thrombus in the A-V Shunt of the control rats, the thrombus formation suppression rate, (5)) were calculated.

TABLE 7

| | | | Thrombus | | | |
|---|---|---|---|---|---|---|
| | | Number | Wet Condition | | Dry Condition | |
| Treatment | Dosage (mg/kg/day) | of Rats | Weight (mg) | Suppression Rate (%) | Weight (mg) | Suppression Rate (%) |
| Control | — | 7 | 47.35 ± 5.847 | — | 12.64 ± 1.425 | — |
| Ticlopidine (T) | 50 | 8 | 35.03 ± 9.167** | 26 ± 19 | 9.53 ± 2.60* | 25 ± 21 |
| Ticlopidine (T) | 100 | 5 | 30.45 ± 4.721*** | 36 ±10 | 8.78 ± 1.503** | 31 ± 12 |
| T + Ginkgo biloba Extracts | 50 + 20 | 8 | 29.06 ± 8.363*** | 39 ± 18 | 8.04 ± 2.489*** | 36 ± 20 |
| T + Ginkgo biloba Extracts | 50 + 40 | 6 | 26.13 ± 6.422*** | 45 ± 14 | 7.39 ± 2.212*** | 42 ± 17 |

(Note)
*$P < 0.05$,
**$P < 0.01$,
***$P < 0.001$, Statistical significance

As shown in the Table 7, when 50 mg/kg or 100 mg/kg of ticlopidine was administered alone, the thrombus formation suppression rates were 26% (wet), 25 (dry), and 36% (wet), 31% (dry), respectively. When 50 mg/kg of ticlopidine and 20 mg/kg of Ginkgo biloba extract were administered in combination, the thrombus formation suppression rates of 39% (wet), and 36% (dry) were recorded, which were significant improvement of the suppression effect on the platelets aggregation from the results shown in the individual administration. The results in the combined administration group were similar to those shown in the administration of 100 mg/kg of ticlopidine Further, when 50 mg/kg of ticlopidine and 40 mg/kg of Ginkgo biloba extract were administered in combination, the thrombus formation suppression rates of 45% (wet), and 42% (dry) were recorded, which were far superior than those of the individual administration of 100 mg/kg of ticlopidine.

Experiment 4

The Effect on Platelet Aggregation in the A-V Shunt of Rats

After the administration of the same regimens used in Experiment 3 for the duration of 9 days, the weights of thrombus formations at the A-V Shunt were measured as the sample of the blood therefrom was collected for the purposes of studying the effect on the ex vivo platelet aggregation after the AV-Shunt. In particular, to the PRP (supernatant after the centrifuge of the blood sample for 10 minutes at 200×g) prepared from the respective blood sample, ADP $3\times10^{-5}$M, which is the platelets aggregation inducer, were added for the purposes of inducing aggregation.

The platelets of the rats with the A-V Shunt were more active than those in the control group. In order to study the ex vivo platelet aggregation effect of the rats' blood without A-V Shunt, the concentration of ADP lower than $1\times10^{-5}$M was used. With the maximum platelet aggregation rate of rats in the control group with A-V Shunt set at 100, various aggregation rates were compared. The results are shown in the Table 8.

The above time intervals were shorter than the time interval for the maximum aggregation of platelets of 1.8 minutes and the total aggregation time of 4.0 minutes in the case where 50 mg/kg of ticlopidine and 40 mg/kg of Ginkgo biloba extract were administered in combination.

Experiment 5
Prolongation of the Bleeding Time

The regimens of ticlopidine and Ginkgo biloba extract were administered onto female rats for the duration of 5 days. One hour after the final administration of the regimen, 250 mg/kg of ketamine was injected into muscle tissue for anesthesia. 2 mm from the tail end was incised with the razor blade, after which the blood therefrom was blotted with the filter paper at the interval of 5 second to the point of the hemorrhage stoppage. The respective time was recorded and shown in Table 9.

TABLE 8

| Treatment | Dosage (mg/kg/day) | Number of Rats | Aggregation Rate (%) | | | Time (Minute) | |
|---|---|---|---|---|---|---|---|
| | | | Maximum | 2 Minutes | 3 Minutes | Maximum | Total |
| Control | — | 6 | 100 | 97.7 ± 1.3 | 89.4 ± 18.4 | 2.4 ± 0.3 | 5.7 ± 1.3 |
| Ticlopidine (T) | 50 | 8 | 78.2 ± 12.2 | 74.4 ± 16.8** | 45.8 ± 27.2 | 1.8 ± 0.3** | 4.33 ± 1.2 |
| Ticlopidine (T) | 100 | 7 | 72.6 ± 8.6 | 62.9 ± 14.8*** | 21.4 ± 22.9 | 1.5 ± 0.2*** | 3.4 ± 0.7** |
| T + Ginkgo biloba Extracts | 50 + 20 | 5 | 67.0 ± 18.1 | 58.1 ± 26.6** | 27.0 ± 27.4 | 1.6 ± 0.3** | 3.4 ± 0.8* |
| T + Ginkgo biloba Extracts | 50 + 40 | 7 | 71.0 ± 17.7 | 64.3 ± 24.0**** | 38.3 ± 33.9 | 1.8 ± 0.5* | 4.00 ± 1.5 |

(Note)*: $P < 0.05$, : $P < 0.01$, *: $P < 0.001$, Statistical Significance

The maximum aggregation occurred in 2.4 minutes after the ADP was added to the PRP in the control group. 3 minutes thereafter, 89% aggregation rate was maintained. It took 5.7 minutes for the complete de-aggregation.

On the other hand, as for the rats with the single administration of 50 mg/kg or 100 mg/kg of ticlopidine, the maximum aggregation were 78% and 72% of that of the control group. At the intervals of 2 and 3 minutes, the aggregation rates were 74%, 45 %, 62 %, 21 %, respectively. As time passed, the aggregation rates were becoming significantly lower as compared to that of the control group. Further, with respect to the groups in which 50 mg of ticlopidine and 20 mg of Ginkgo biloba extract (5:2) were administered in combination, the maximum aggregation rates, and those at 2 and 3 minute intervals were 67%, 58% and 27%, respectively, which are similar to the results shown in the 100 mg group. However, with respect to the groups in which 50 mg of ticlopidine and 40 mg of Ginkgo biloba extract (5:4) were administered in combination, the maximum platelet aggregation rates, and those at 2 and 3 minute intervals were all higher than those in the group with 50 mg of ticlopidine and 20 mg of Ginkgo biloba extract.

As for the time interval for the formation of the maximum aggregation and the complete de-aggregation, they were shorter in the 100 mg group than in the 50 mg group for the individual administration. When 50 mg of ticlopidine and 20 mg of Ginkgo biloba extract were administered in combination, the time intervals were 1.6 minutes and 3.4 minutes, respectively, which are similar to the time intervals in the individual administration of 100 mg of ticlopidine.

TABLE 9

| Treatment | Dosage (mg/kg/day) | Number of Rats | Time (Second) |
|---|---|---|---|
| Control | — | 6 | 1028 ± 335* |
| Ticlopidine (T) | 50 | 6 | 1546 ± 332* |
| Ticlopidine (T) | 100 | 6 | 2023 ± 872* |
| T + Ginkgo biloba Extracts | 50 + 20 | 6 | 1528 ± 377* |
| T + Ginkgo biloba Extracts | 50 + 40 | 6 | 2480 ± 921* |

(Note)
*$P < 0.05$, Statistical significance

As shown in Table 9, the bleeding time for the 50 mg/kg group increased 1.5 times from that in the control group in which only the arabic gum was applied. Further, the bleeding time for the 100 mg/kg group increased 2 times from that in the control group. When 50 mg/kg of ticlopidine and 20 mg/kg of Ginkgo biloba extract were administered in combination, the corresponding time interval increased front that in the control group but did not increase from the time for interval for 50 mg/k group. However, when the Ginkgo biloba extract were administered in combination in the ratio of 5 to 4, the time interval was prolonged from that of the 100 mg/kg individual administration of ticlopidine.

Consequently, when the Ginkgo biloba extract were administered in combination, the dosage amount of ticlopidine can be reduced without compromising the effectiveness thereof.

Experiment 6

A change in the Ratio of the Neutrophil, Eosinophil, Basophil, Macrophage and Lymphocytes after the 16 Week of the Administration of the Pharmaceutical Composition For the purposes of revealing the effects of the pharmaceutical composition under said invention, the following reagents and apparatus were used to carry out the administration experiments:

Centrifuge, CBC Bottle, 5 ml, glass tube+Heparin (200U/ml) 29 $\mu$l/tube, 2 ml Ephendorph tube, 3 ml syringe+21 G needle 10 ml syringe, saline solution, cytometer, slide glass, 10 % formalin solution, Coulter counter (Coulter Electronics Inc., Hialeah, Fla. 33010, and Mississauga, Ontario) Microtome, HPLC-UV Chromatography (Kontron 420, Supelco Inc. Bellefonte, Pa.).

In addition as for the laboratory animals used in the experiment herein, 6 week-old rats weighing 60 g each (Spraque-Dawley) were purchased and kept at 23° C. and 50% humidity with ad libitum feeds and water. These rats were divided into the control group the ticlopidine administration group, and the ticlopidine+Ginkgo biloba extract administration groups in a variation ratio of 5:1, 5:2, and 5:4.

The changes due to the dosage amount and blending ratio were set as follows. In terms of the clinical application, one ticlopidine tablet is 200 mg or 250 mg with a daily dosage of 200 mg to 600 mg. On the other hand, one tablet of the Ginkgo biloba extract is 40 mg, 80 mg, 120 mg with a daily dosage of 120 mg to 240 mg. The blending ratios of ticlopidine and Ginkgo biloba extract were 5 to 1, 5 to 2, and 5 to 4.

TABLE 10

| Treatment | Dosage (mg/kg/day, P.O.) | Drug concentration in drinking water (mg/ml) | Number of Rats |
| --- | --- | --- | --- |
| Control | — | — | 10 |
| Ticlopidine (T) | 300 | 300/250 | 10 |
| T + Ginkgo biloba Extracts (5:1) | 300 + 60 | 300 + 60/250 | 10 |
| T + Ginkgo biloba Extracts (5:2) | 300 + 120 | 300 + 120/250 | 10 |
| T + Ginkgo biloba Extracts (5:4) | 300 + 240 | 300 + 240/250 | 10 |

Using said reagents and apparatus, ticlopidine individually or in combination with the Ginkgo biloba extract in the ratios of 5:1, 5:2 and 5:4 were orally administered onto 6 week-old rats for the duration of 16 weeks. After anesthesia, blood was collected through the abdominal aorta, and the number of white blood cells were counted using the Coulter Counter. Using the cytochemical dyeing method, the ratios of neutrophil, eosinophil, basophil, macrophage and lymphocytes were measured. The results are shown in Table 11.

TABLE 11

Effects of Ticlopidine Administration for 16 Weeks Alone or in Combination with Ginkgo Ext. on the Number of Leukocytes in Rat

| Drug Treatment | Rat No | Total Leukocyte ($\times 10^3/\mu l$) | Neutrophil (%) | Eosinophil (%) | Basophil (%) | Macrophage (%) | Lymphocyte (%) |
| --- | --- | --- | --- | --- | --- | --- | --- |
| Control | 8 | 10.9 ± 1.6 | 14.3 ± 1.5 | 2.2 ± 0.4 | 1.4 ± 0.3 | 7.0 ± 1.2 | 75.1 ± 2.1 |
| Ticlopidine | 8 | 9.3 ± 1.3 | 10.5 ± 1.1* | 2.0 ± 0.4 | 1.7 ± 0.2 | 5.5 ± 0.8 | 80.4 ± 1.6 |
| Ticlo. + Ging (5:1) | 8 | 12.4 ± 1.1 | 12.9 ± 0.8 | 1.2 ± 0.2 | 0.8 ± 0.1 | 4.5 ± 0.5 | 80.7 ± 0.7 |
| Ticlo. + Ging (5:2) | 8 | 10.0 ± 0.6 | 15.0 ± 1.8# | 2.2 ± 0.3 | 0.9 ± 0.3 | 4.3 ± 0.4 | 77.6 ± 2.3 |
| Ticlo. + Ging (5:4) | 8 | 14.5 ± 2.7 | 13.6 ± 1.9 | 2.8 ± 0.4 | 0.7 ± 0.2 | 4.5 ± 0.6 | 78.5 ± 2.5 |

Each data represents mean ± S.E.
*: $P < 0.05$: Significantly different from normal group.
: $P < 0.05$: Significantly different from ticlopidine treated group As a result, when ticlopidine was administered for the duration of 16 weeks, the white blood cells in the blood showed a slight tendency of a decrease from that in the control group, but there was not a statistical significant difference. Further, when ticlopidine and Ginkgo biloba extract were administered in combination at a ratio of 5:1 5:2, 5:4 for the duration of 16 weeks, there was not a significant difference from that in the control group or that in the individual ticlopidine group.

On the other hand, with respect to eosinophil, basophil, macrophage or lymphocyte, when ticlopidine or Ginkgo biloba extract were administered individually or in combination at the ratios of 5:1, 5:2, 5:4 for the duration of 16 weeks, there were not significant differences from that of the control group.

However, in the case of neutrophil, whereas the normal rats showed 14.3±1.5%, the group with the ticlopidine alone administration decreased to 10.5±1.1% ($P<0.05$). When ticlopidine and Ginkgo biloba extract were administered in combination of 5:2 for the duration of 16 weeks, the result was 15.0±1.8% ($P<0.05$), which was a significant recovery from that of the individual administration of ticlopidine.

Experiment 7

Change in the Numbers of Leukocytes, and the Ratios of Neutrophil, Eosinophil, Basophil, Macrophage or Lymphocyte after 16 Weeks of the Drug Administration Followed by Two Weeks of Withdrawal Rats were administered with the same regimens as in Experiment 6 for the duration of 16 weeks, and those with two weeks of withdrawal were separately maintained. In particular, as shown in Table 12, the 6 week-old rats were divided into the control group, the ticlopidine administration group, and the group in which ticlopidine+Ginkgo biloba extract were administered in combination (5:2). After 16 weeks of treatment followed by two weeks of withdrawal, the number of leukocyte, and the ratios of neutrophil, eosinophil, basophil, macrophage and lymphocyte were measured using the same method as in Experiment 6.

TABLE 12

| Treatment | Dosage (mg/kg/day, P.O.) | Drug Concentration in Drinking Water | Number of Rats | Remark |
|---|---|---|---|---|
| Control | — | — | 8 | — |
| Ticlopidine (T) | 300 | 300 mg/250 ml | 8 | Withdrawal after 16 weeks of treatment |
| T + Ginkgo biloba Extracts (5:2) | 300 + 120 | 300 + 120 mg/250 ml | 8 | Withdrawal after 16 weeks of treatment |

The results of the measurements are shown in Table 13.

TABLE 13

Effects of 2 Weeks of Withdrawal after 16 Weeks of Treatment of Ticlopidine Alone or in Combination with Ginkgo Ext. on the Number of Leukocytes in Rat

| Drug Treatment | Rat No. | Total Leukocyte ($\times 10^3/\mu l$) | Neutrophil (%) | Eosinophil (%) | Basophil (%) | Macrophage (%) | Lymphocyt (%) |
|---|---|---|---|---|---|---|---|
| Normal | 8 | 12.6 ± 1.6 | 14.1 ± 1.3 | 2.0 ± 1.0 | 0.7 ± 0.2 | 5.6 ± 0.6 | 77.7 ± 1.3 |
| Ticlopidine | 8 | 10.3 ± 1.2 | 15.9 ± 1.7* | 2.7 ± 0.2 | 0.3 ± 0.1 | 3.5 ± 1.0 | 77.8 ± 0.5 |
| Ticlo. + Ging (5:2) | 8 | 11.9 ± 1.7 | 15.0 ± 2.2 | 1.8 ± 0.3 | 1.2 ± 0.3 | 4.0 ± 1.2 | 77.9 ± 3.9 |

Each data represents mean ± S.E.

When ticlopidine was orally administered for the duration of 16 weeks as in Table 11, the total number of white blood cells showed a decreasing tendency where as the number of neutrophils showed a significant decrease. When ticlopidine was orally administered for the duration of 16 weeks followed by two weeks of withdrawal, the number of the neutrophil showed a normal recovery as in the control group. Further, when ticlopidine and Ginkgo leaf extracts were administered in combination at a ratio of 5:2, the results therefrom were similar to those in the control group and the ticlopidine alone administered group.

Experiment 8

A Change in the Number of Bone Marrow Cells after the Administration of the Pharmaceutical Composition for the Duration of 16 Weeks.

For the purposes of measuring the reduction of the white blood cell precursors at the marrow due to ticlopidine, ticlopidine alone or in combination with Ginkgo biloba extract were administered onto the 6 week-old rats at ratios of 5:1, 5:2, 5:4 for the duration of 16 weeks. Thereafter, the number of bone marrow cells was measured.

In detail, for the purposes of measuring the numbers of the precursor cells of leukocytes, the femur part was incised with the elimination of the surrounding muscle tissues. Then, both sides of epiphysis were incised, from which approximately 2 cm of femur was obtained. The matter was flush with 1 ml of saline using the 3 ml syringe (21G). Then, the perfusate was collected with the Ephendorph tube and centrifuged at 2,000 rpm for 5 minutes. After removing the supernatant, 1 ml of the Turks solution comprising 10% acetic acid and the dye for white blood cells was added to the precipitated cell layer. Thereafter, the tube was gently mixed and centrifuged at 2,000 rpm for 5 minutes. After removing the supernatant, 1 ml of saline solution was added to the precipitated cell layer. One again, the tube was gently mixed, and centrifuged at 2,000 rpm for 5 minutes, after which the cells were washed. Then, removing the supernatant once again, 0.5 ml of saline solution was added to the precipitated cell layer and mixed. The drop therefrom was added to the Cytometer, and the number of cells in the RRRRR 5 part (4 corners and the center) was counted. Using the following formula, the number of marrow cells were calculated: Counted Number×50×10×10$^3$=Number of white blood cell precursor/femur.

The numbers of marrow cells at femur are shown in FIG. 1. In particular, when ticlopidine was repeatedly administered for the duration of 16 weeks, the number of white blood cell precursor at marrow showed a significant reduction from that in the control group. On the other hand, when ticlopidine and Ginkgo biloba extract were administered in combination at a ratio of 5 to 2 during the 16 week period, the number showed a significant recovery as compared to that in the individual administration of ticlopidine.

Further, when ticlopidine and Ginkgo biloba extract were orally administered in combination at a ratio of 5 to 1 or 5 to 4 during the 16-week period, the number showed an increasing tendency from that in the individual administration but without a significance difference. The results herein showed the same tendencies as in the aforementioned changes in the number of neutrophil.

Experiment 9

Figure 2:
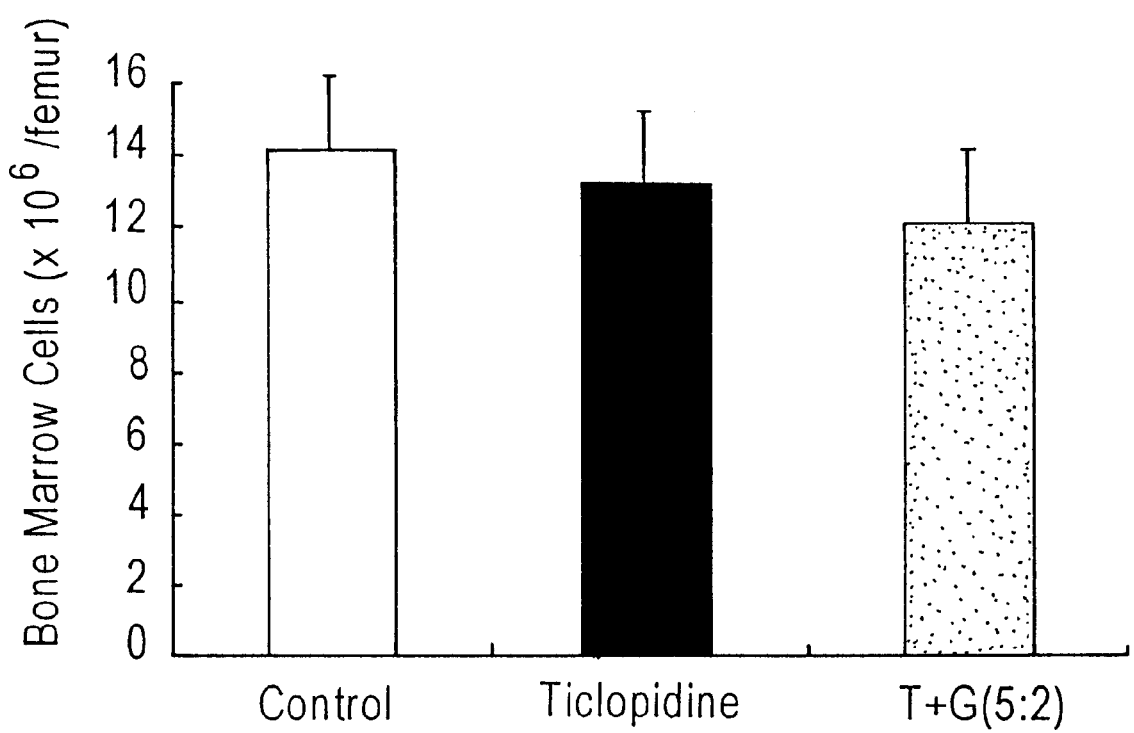
FIG. 2 is the graph showing the effects of the single use of ticlopidine, and the combination use of ticlopidine and Ginkgo biloba extract on the number of femur marrow cells of the rats after the 16-week period of treatment followed by two weeks of withdrawal.
Figure 3A:
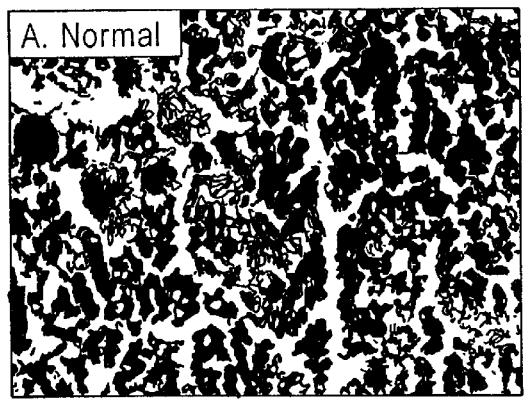
FIG. 3 is the photograph (×400) of the control group and the histology of the femur osteoepiphysis marrow cells of the white mice when ticlopidine is used alone or in combination (5:1, 5:2, 5:4) with the Ginkgo biloba extract during the 16-week period.
Figure 3B:
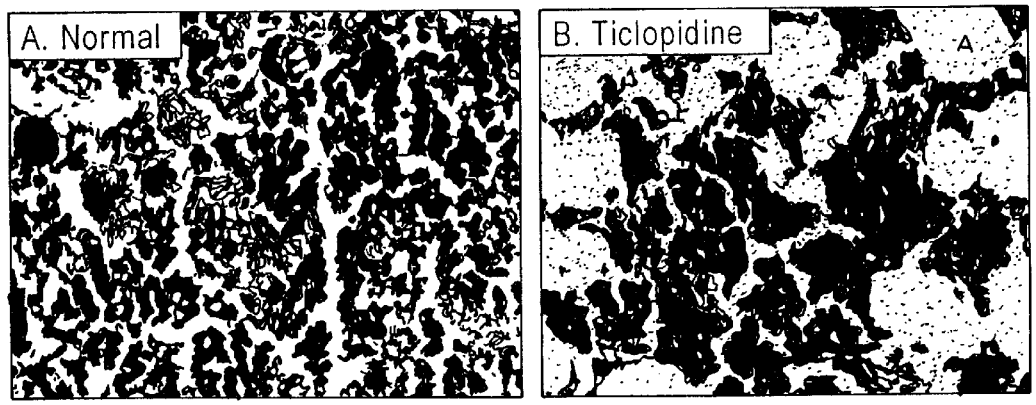
Figure 3C:
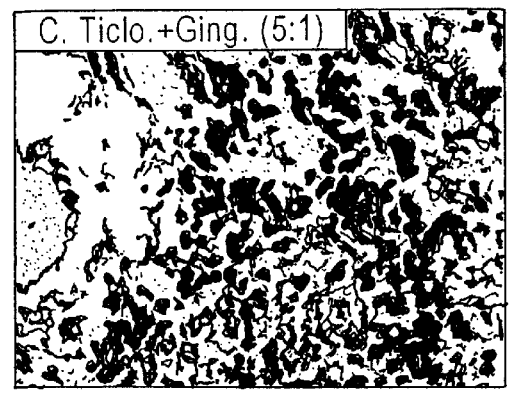
Figure 3D:
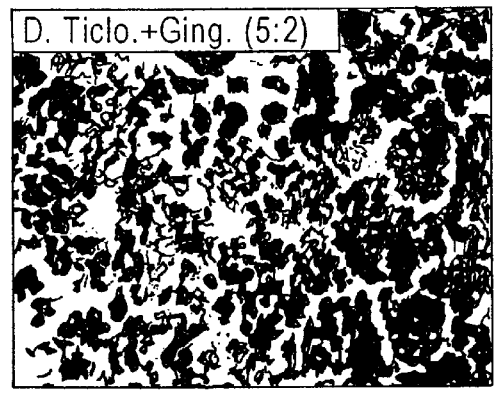

The Changes in the Number of the Bone Marrow Cells after 16 Weeks of the Administration of the Pharmaceutical Composition, Followed by 2 Weeks of Withdrawal Using the same method as in the Experiment 8, ticlopidine alone or in combination with Ginkgo biloba extract were administered onto the 6 week-old rats at the ratios of 5:2 for the duration of 16 weeks followed by 2 weeks of withdrawal. Thereafter, the number of bone marrow cells at femur was measured. The results therefrom are shown in FIG. 2.

As shown in FIG. 1, the numbers of marrow cells decreased significantly when ticlopidine was orally administered for the 16-week duration while the number for the combined administration was similar to that of the control. On the other hand, when ticlopidine was repeatedly administered for 16 weeks, followed by 2 weeks of withdrawal, the number of marrow cells at femur recovered to the normal level. Further, when ticlopidine and Ginkgo biloba extract were administered in combination, the numbers were similar to those of the control and those of the group in which ticlopidine was administered alone.

Experiment 10
Histological Examination of the Marrow Cells after the Administration of the Pharmaceutical Composition for 16 Weeks For the purposes of measuring the reduction of the number of white blood cell precursors at the marrow due to ticlopidine, ticlopidine alone or in combination with Ginkgo biloba extract were administered onto the 6 week-old rats at ratios of 5:1, 5:2, 5:4 for the duration of 16 weeks. Thereafter, the marrow cells was histologically examined.

In detail, for the purposes of examining the histology of the marrow cells, the femur of a rat from each group was incised and preserved in the 10% formalin solution. The femur so extracted was decalcified with the decalcification solution and embedded with paraffin after the ordinary course of the histological process. The femur tissue so embedded with paraffin was sliced at a thickness of 4 μm, followed by hematoxylin and eosins. Thereafter, the slide was examined with the light microscope at 400×.

For the case where ticlopidine individually or in combination with Ginkgo biloba extract were administered onto the 6 week-old rats at the ratios of 5:1, 5:2, 5:4 for the duration of 16 weeks, the photograph from the histological examination of the femur marrow cells are shown in FIG. 3.

As compared to that of the control group, the density of the marrow cells in the case of the alone administration of ticlopidine showed malignant vacuolation caused by extravasation of the fat cells. The density of megakaryocyte, the precursor of the platelet, decreased at epiphysis as compared to that in the control group. Within white blood cell precursors, the density of myelocytes in the growth stage significantly decreased while that of the band-granulocyte, the matured white blood cells, showed no change.

On the other hand, when ticlopidine and Ginkgo biloba extract were administered in combination, the density thereof was similar to that of the control group due to the lack of malignancy. As for the 5:4 group, there was an insignificant decrease in terms of density. Other marrow cells were similar to those of the control group with respect to density.

In fact, as compared to the control group, the group in which only ticlopidine was administered showed atrophy of marrow cells, namely, an increase in vacuolation and reduction in density. The reduction of density of mylecyote, the precursor of the white blood cells, is deemed to be a change in suppression effect with respect to neutropenia.

When ticlopidine and Ginkgo biloba extract were administered in combination, there were no significant changes depending on the ratio. However, with respect to the 5:2 group, the marrow density and cell composition were similar to that of the control group.

Experiment 11

Histological Examination of the Marrow Cells after the Administration of the Pharmaceutical Composition for 16 Weeks, Followed by 2 Weeks of Withdrawal For the purposes of measuring the reduction of the number of white blood cell precursor at the marrow due to ticlopidine, ticlopidine alone or in combination with Ginkgo biloba extract were administered onto the 6 week-old rats at ratios of 5:1, 5:2, 5:4 for the duration of 16 weeks, followed by 2 weeks of withdrawal. Thereafter, the marrow cells were histolosically examined.

Further, in the group in which ticlopidine was administered for 16 weeks followed by 2 weeks of withdrawal, the density of the marrow cells was similar to that of the control group due to lack of malignancy (refer to Table 15 and FIG. 4).

TABLE 14

Effects of Ticlopidine Administration for 16 Weeks Alone or in Combination with Ginkgo Ext. on the Number of Leukocytes in Rat

| Drug Treatment | Cellularity | Megakaryocyte | Erythro progenitor cell | Myelocyte | Band-granulocyte | Monocyte |
|---|---|---|---|---|---|---|
| Normal | ++ | ++ | + | ++ | ++ | + |
| Ticlopidine | + | + | + | + | ++ | − |
| Ticlo. + Ging (5:1) | ++ | ++ | + | ++ | ++ | + |
| Ticlo. + Ging (5:2) | +− | ++ | + | ++ | ++ | + |
| Ticlo. + Ging (5:4) | +/−+ | ++ | + | ++ | ++ | + |

TABLE 15

Effects of 2 Weeks of Withdrawal of Ticlopidine Administration for 10 Weeks Alone or in Combination with Ginkgo Ext. on the Number of Leukocytes in Rat

| Drug Treatment | Cellularity | Megakaryocyte | Erythro progenitor cell | Myclocyte | Band-granulocyte | Monocyte |
|---|---|---|---|---|---|---|
| Normal | ++ | ++ | + | ++ | ++ | + |
| Ticlopidine | + | + | + | ++/+++ | ++ | − |
| Ticlo. + Ging (5:2) | ++ | +/++ | + | +/++ | ++ | −/+ |

Further, as for the myelocytes in the growth stage among the white blood precursor cells with respect to the combined administration, there was a concrete trend of an increase as compared to that of the individual administration. Consequently, when ticlopidine is administered for 16 weeks followed by 2 weeks of withdrawal, there was a trend of a recovery as shown by the disappearance of atrophy and an increase in myelocytes.

Further, density of megakaryocyte at femur, which is the precursor of the platelet, increased almost to the point of the control group. In contrast, when ticlopidine and the Ginkgo biloba extract were administered in combination at a ratio of 5:2 followed by 2 weeks of withdrawal, there was a slight decrease in myelocyte.

Experiment 12
CFU-C Analysis

The marrow cells were separated from the mouse femur. Then, with the Percoll reagent of 1.1 specific gravity, the mononuclear cells in the marrow cells were separated into 3 layers consisting of specific gravity of 1.090, 1.075 and 1.063, respectively. The cells were respectively separated using the density gradient centrifuge. Specifically, the layer of marrow cells was placed in the 25 ml centrifuge tube, and 20 ml of said solution was poured in, during which 3 layers were formed. The tube was centrifuged at 4° C., 2,000 rpm for 30 minutes. Thereafter, the marrow cells were obtained from the center layer thereof. T-lymphocytes were removed by means of the E-rosette production method, which uses the sheep red blood cells. The cells so obtained were washed with the Hank balanced salt solution (HBSS) three times and dispersed onto the Iscove modified Dubecco medium (IMDM GIBCO).

In the culture medium, the effect of ticlopidine on the colony-forming unit in culture (CFU-C) was tested as follows: The $2 \times 10^5$ of marrow cells were suspended and cultured in 1 ml of IMDM containing 0.3% Agar (DIFCO), 15% bovine fetal serum (GIBCO), 100 U of granulocyte-macrophage colony-stimulator (CSF-CHUGAI), 0.02 ml of ticlopidine individually or in combination with the Ginkgo biloba extract At this point, the concentration of ticlopidine was 30ng/ml.

Further, as against the concentration of 30ng/ml of ticlopidine, the Ginkgo biloba extract in the ratios of 5:1, 5:3, 5:4 were used in combination, after which the cells were cultured in the incubator with 5% $CO_2$, 37° C., and 100% humidity for 10 days. At this point, the number of colonies consisting of 50 or more cells were counted using the inverted microscope, and the cell suppression effects in percentage as compared to those in the control group were calculated.

Figure 5:
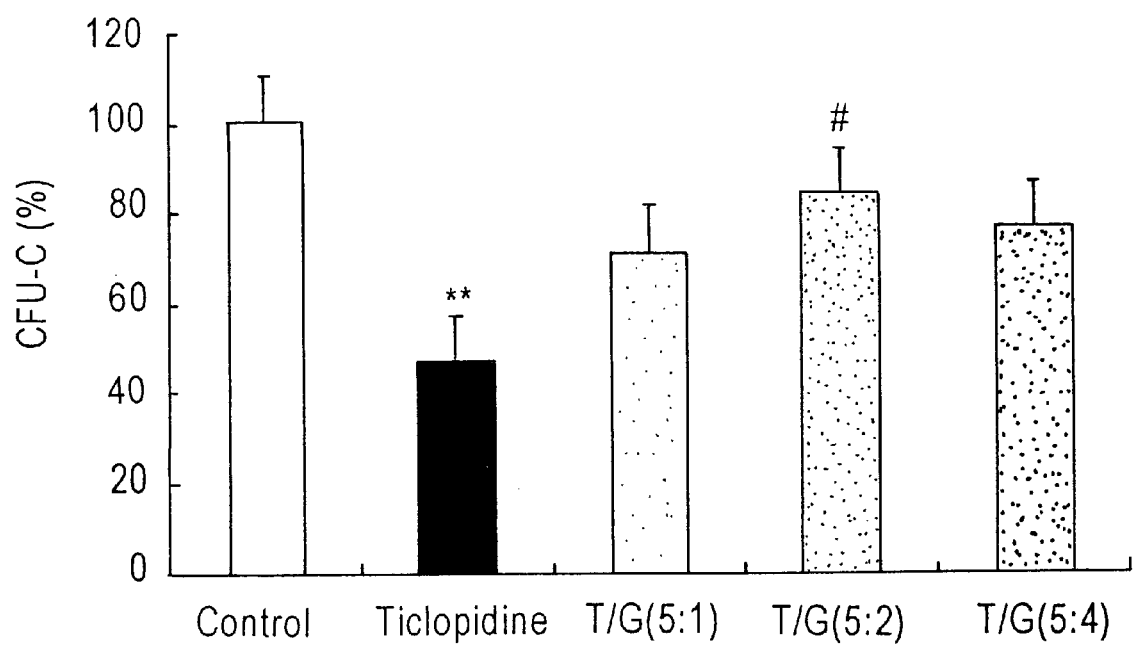
FIG. 5 is the bar graph showing, the effects on the suppression of the CFU-C induced by ticlopidine (30 mg/ml) when ticlopidine is used alone or in combination with the Ginkgo biloba extract.

Meanwhile, in the case where 30 ng/ml of ticlopidine which showed approximately 50% suppression effect as against the CFU-C, was used in combination with Ginkgo biloba extract in the ratios of 5:1, 5:2, 5:4, the changes in CFU-C are shown in FIG. 5. When, ticlopidine and Ginkgo biloba extract were used in the ratio of 5:1 and 5:4, there was no significant difference compared to those of the ticlopidine alone treated group. However, when ticlopidine and Ginkgo biloba extract were used in the ratio of 5:2, the suppression effect was increased significantly with the similar trend of a recovery with that of the control group.

The aforementioned results coincided with those of the in vivo tests in which the decrease in the numbers of neutrophil and marrow cells came about from the oral administration of the ticlopidine for 16 weeks. Further, with respect to the administration of the ticlopidine and Ginkgo biloba extract in the ratio of 5:2, the results as above coincided with the test results of the recovery to the similar level of the control group.

Figure 6:
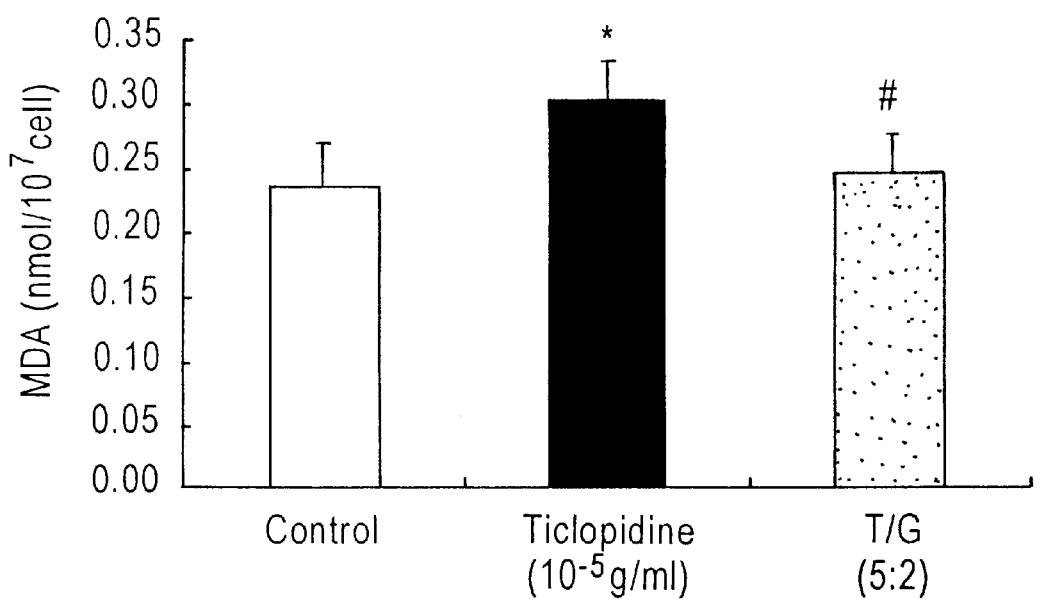
FIG. 6 is the bar graph showing the effects on the lipid-peroxide induced by hydrogen peroxide from the marrow cells when ticlopidine ($10^{-4}$ M) is used alone or in combination with the Ginkgo biloba extract (5:2).

Experiment 13
The Measurement of Lipid Peroxidation with Respect to Marrow Cells The part of femur of a rat was incised, and the surrounding muscle tissue was removed therefrom in order to obtain the femur. The matter was flush with 1 ml of saline using the 3 ml syringe. Then, the perfusate was collected with the tube and centrifuged at 3,000 rpm for 15 minutes. After removing the supernatant the deposited marrow cells were dispersed onto IMDM and were diluted to $10^7$ cell/ml by means of measuring the number of cells with hemocytometer. The cells were divided into 3 groups, namely, the control, ticlopidine treatment, and ticlopidine+Ginkgo biloba extract group (5:2). To the control group, 10 mmol/l, of $H_2O_2$, 20 $\mu$l of the same as added. To the ticlopidine treatment groups, $10^{-5}$ g/ml was added. To the ticlopidine+Ginkgo biloba extract combination group, $10^{-5}$ g/ml of ticlopidine and $4 \times 10^{-6}$ g/ml of Ginkgo biloba extract were added. All three groups were cultured for 1 hour at 37° C. Thereafter, the level of lipid-peroxide in the marrow cells was measured by means of the TBA method. In particular, the amount of malondialdehyde produced from the reaction with the TBA sample solution was measured with spectrophotometer, and the results are shown in FIG. 6. The TBA measurement of the control group was 0.23±0.02 whereas that of the ticlopidine ($10^{-5}$ g/ml) treatment group was 0.30±02, the difference of which clearly suggests a cell damage by ticlopidine. Nevertheless, when the Ginkgo biloba extract ($4 \times 10^{-6}$ g/ml) were used in combination, the result was 0.24±0.01, which was similar to that of the control group and a significant reduction from the results of the individual administration of the ticlopidine. Hence, by means of anti-oxidation effect, the Ginkgo biloba extract is deemed to suppress cell damage due to ticlopidine.

From the Experiment 6 to 13, 100 weight parts of ticlopidine (approximately 300 mg/kg/day) were dissolved in the drinking water and so administered to 6 week-old rats for 16 weeks. Thereafter, the existence of a neutropenia toxicity in blood and marrow was confirmed. Further, the Ginkgo biloba extract with the anti-oxidant effect was used in combination at the respective ratios of 20, 40, 80 weight parts, and the reduction of neutropenia was measured. After 16 weeks of the ticlopidine administration, neutropenia including a reduction of marrow cells and myelocytes, which is the precursor to the white blood cells, were detected.

The aforementioned suppression effect returned to the normal level after 16 weeks of ticlopidine administration followed by 2 weeks of withdrawal. In addition when Ginkgo biloba extract in 40% weight parts of ticlopidine were administered in combination, the reduction in marrow cells, namely neutropenia, returned to the level similar to that of the control group. However, in the case of the combined administration of ticlopidine and the Ginkgo biloba extract in 20 or 80 weight parts, there was no significant suppression effect.

Meanwhile, when the suppression effect on cell growth was measured by culturing the granulocyte precursor cells in the in vitro tests, the ticlopidine showed cytotoxicity via dosage-dependent suppression effect. Yet, in the case of the combined administration with Ginkgo biloba extract, there was a reduction in the suppression effect. Further, the cytotoxicity increased due to ticlopidine in the in vitro tests via oxidation reaction with peroxidase in the marrow cells but decreased for the combined administration with Ginkgo biloba extract.

The results as above show that ticlopidine causes neutropenia via cytotoxicity on the neutrophil precursor cells and that the Ginkgo biloba extract with the anti-oxidant effect suppresses such toxicity caused by ticlopidine. In particular, the administration of 100 weight parts of ticlopidine as against 40 weight parts of Ginkgo biloba extract have shown to be the most effective in the in vivo tests.

In sum, when ticlopidine is administered in combination with the Ginkgo biloba extract, there is powerful anti-thrombotic and anti-aggregation effects as compared to the individual administration of ticlopidine although there is a slight discrepancy in the results depending on the dosage, duration and measurement method. Consequently, by using the Ginkgo biloba extract in combination with ticlopidine, the dosage of ticlopidine is expected to be reduced in coinunction with minimizing the side-effects of the ticlopidine.

What is claimed is:

1. A composition comprising a combination of anti-thrombotic effective amounts of ticlopidine and Ginkgo biloba extract, wherein the proportions of said ticlopidine and Ginkgo biloba, respectively, reduce the risk of neutropenia and agranulocytosis that would otherwise have been caused by the administration of said ticlopidine in the absence of said Ginkgo biloba.

2. The composition claimed in claim 1 comprising 10 to 240 parts of Ginkgo biloba extract per 100 parts of ticlopidine.

3. A dosage therapeutic composition comprising the composition as claimed in claim 1 in admixture with a pharmaceutically acceptable carrier.

4. A dosage therapeutic composition as claimed in claim 1 comprising about 50 to 600 mg of ticlopidine and about 20 to 240 mg of Ginkgo biloba extract.

5. A method of treating diseases induced by thrombosis which comprises administering an anti-thrombotic effective amount of a mixture of ticlopidine and Ginkgo biloba extract, wherein the proportions of said ticlopidine and Ginkgo biloba, respectively, reduce the risk of neutropenia and agranulocytosis that would otherwise have been caused by the administration of said ticlopidine in the absence of said Ginkgo biloba.

6. The method as claimed in claim 5 wherein said disease is at least one selected from the group consisting of cerebral ischemic disease, ischemic heart disease, chronic arterial occlusion and post operative thrombo embolic events.

7. The method as claimed in claim 5 wherein said administration occurs after blood vessel or subarachnoid hemorrhage surgery.

8. The dosage therapeutic composition as claimed in claim 3 in the form of a tablet, vesicant, granule or capsule.

* * * * *